(12) United States Patent
Freeman et al.

(10) Patent No.: US 10,661,035 B2
(45) Date of Patent: May 26, 2020

(54) INHALATION DEVICE WITH CONSTRICTED FLOW PATHWAY

(71) Applicant: INDOSE INC., Woodland Hills, CA (US)

(72) Inventors: Daniel Freeman, Agoura, CA (US); Ari Freeman, Lafayette, CA (US)

(73) Assignee: INDOSE INC, Woodland Hills, CA (US)

( * ) Notice: Subject to any disclaimer, the term of this patent is extended or adjusted under 35 U.S.C. 154(b) by 0 days.

(21) Appl. No.: 16/382,366

(22) Filed: Apr. 12, 2019

(65) Prior Publication Data

US 2019/0261691 A1    Aug. 29, 2019

Related U.S. Application Data

(63) Continuation of application No. 16/249,477, filed on Jan. 16, 2019.
(Continued)

(51) Int. Cl.
*A61M 15/00* (2006.01)
*A61M 15/06* (2006.01)
(Continued)

(52) U.S. Cl.
CPC ............. *A61M 15/008* (2014.02); *A24F 7/00* (2013.01); *A24F 47/008* (2013.01); *A61M 15/0001* (2014.02); *A61M 15/0065* (2013.01); *A61M 15/0066* (2014.02); *A61M 15/0085* (2013.01); *A61M 15/06* (2013.01); *G01F 13/006* (2013.01); *H05B 1/0297* (2013.01); *A61M 2205/3334* (2013.01);
(Continued)

(58) Field of Classification Search
CPC .. A24F 7/00; A24F 40/10; A24F 40/51; G01F 13/006; A61M 15/0001; A61M 15/0065; A61M 2205/3334; A61M 2205/52
USPC .................................... 131/273, 338; 604/58
See application file for complete search history.

(56) References Cited

U.S. PATENT DOCUMENTS 4,253,508 A  *  3/1981  Bodai .................... A24D 3/045
                                                     131/202
4,474,191 A  *  10/1984  Steiner ..................... A24D 1/00
                                                     131/198.2
(Continued)

*Primary Examiner* — Timothy A Stanis
*Assistant Examiner* — Victoria Murphy
(74) *Attorney, Agent, or Firm* — Sughrue Mion, PLLC; Richard C. Turner

(57) ABSTRACT

An inhalation device includes a light source that emits light, a light sensor that senses an intensity of the light emitted from the light source and a processor or circuit configured to perform a metering process. The metering process may include when a signal indicating that a puff has been detected by the puff detecting element: extracting a predetermined known flow rate that is stored in the memory in advance, determining an amount of vaporized substance that have been produced, and accumulating the determined amount of vaporized substance that has been produced in the memory as a total amount produced. The metering method may also include when the accumulated total amount produced reaches a predetermined threshold: (i) shut off the heating element or (ii) send a signal to an indicator that the predetermined threshold amount of the vaporized substance has been consumed.

19 Claims, 12 Drawing Sheets

Related U.S. Application Data

Figure 1A:
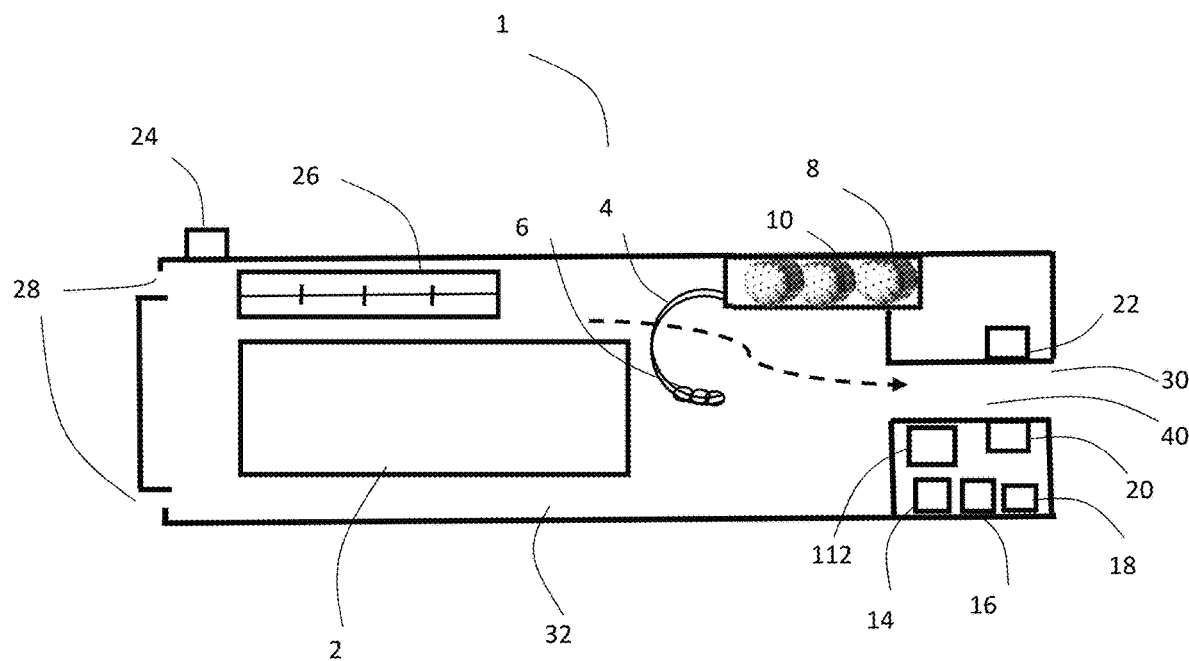

(60) Provisional application No. 62/621,795, filed on Jan. 25, 2018, provisional application No. 62/585,565, filed on Jan. 17, 2018.

(51) Int. Cl.
  *A24F 47/00* (2020.01)
  *A24F 7/00* (2006.01)
  *H05B 1/02* (2006.01)
  *G01F 13/00* (2006.01)
  *G01F 1/05* (2006.01)

(52) U.S. Cl.
  CPC ............ *A61M 2205/3379* (2013.01); *A61M 2205/502* (2013.01); *A61M 2205/52* (2013.01); *A61M 2205/583* (2013.01); *A61M 2205/587* (2013.01); *G01F 1/05* (2013.01)

(56) References Cited

U.S. PATENT DOCUMENTS

| | | | | |
|---|---|---|---|---|
| 4,484,577 A * | 11/1984 | Sackner | ............... | A61K 9/0073 128/200.23 |
| 4,638,820 A * | 1/1987 | Roberts | ................. | A24D 3/041 131/198.2 |
| 5,363,842 A * | 11/1994 | Mishelevich | ........ | A61B 8/0875 128/200.14 |
| 5,388,594 A * | 2/1995 | Counts | ................... | A24F 47/008 128/202.21 |
| 5,392,768 A * | 2/1995 | Johansson | ............. | A61M 15/00 128/200.14 |
| 5,583,790 A * | 12/1996 | Lan | ........................ | B67D 7/303 700/282 |
| 5,842,468 A * | 12/1998 | Denyer | ................ | A61M 15/0086 128/200.23 |
| 5,896,860 A * | 4/1999 | Lockett | ..................... | A24F 1/16 131/209 |
| 6,085,742 A * | 7/2000 | Wachter | ............ | A61M 15/0086 128/200.21 |
| 6,098,618 A * | 8/2000 | Jennings | ........... | A61M 15/0065 128/203.14 |
| 6,234,167 B1 * | 5/2001 | Cox | ................... | A61M 15/0003 128/200.14 |
| 6,606,989 B1 * | 8/2003 | Brand | .................. | A61M 11/005 128/200.16 |
| 2004/0000309 A1 * | 1/2004 | Alston | .............. | A61M 15/0086 128/203.15 |
| 2004/0099266 A1 * | 5/2004 | Cross | ................... | A61M 11/041 128/203.12 |
| 2005/0066962 A1 * | 3/2005 | Altobelli | ........... | A61M 15/0045 128/200.14 |
| 2005/0068528 A1 | 3/2005 | Altobelli et al. | | |
| 2007/0006883 A1 * | 1/2007 | Kolb | .................... | A61M 15/00 128/205.24 |
| 2008/0314384 A1 * | 12/2008 | Harris | ............... | A61M 15/0028 128/203.15 |
| 2009/0056708 A1 * | 3/2009 | Stenzler | ............... | A61M 11/005 128/200.14 |
| 2010/0185183 A1 * | 7/2010 | Alme | ................. | A61M 5/14276 604/891.1 |
| 2012/0285236 A1 * | 11/2012 | Haartsen | .............. | A61M 11/005 73/204.11 |
| 2012/0291781 A1 * | 11/2012 | Kaufmann | .......... | A61M 15/008 128/203.15 |
| 2014/0106324 A1 * | 4/2014 | Adams | ................ | A61M 15/009 434/262 |
| 2015/0272220 A1 * | 10/2015 | Spinka | ................... | A24F 47/008 131/329 |
| 2015/0290417 A1 * | 10/2015 | Stenzler | ............... | A61M 16/085 424/718 |
| 2016/0129182 A1 * | 5/2016 | Schuster | ........... | A61M 5/16831 702/56 |
| 2016/0325055 A1 * | 11/2016 | Cameron | ............. | A61M 11/005 |
| 2017/0030882 A1 * | 2/2017 | Skoda | .................... | G01N 33/15 |
| 2017/0368273 A1 * | 12/2017 | Rubin | .................. | A61M 11/042 |
| 2018/0007965 A1 * | 1/2018 | Karles | ................... | A61M 15/06 |
| 2018/0189458 A1 * | 7/2018 | Shanbhag | ............. | G16H 40/67 |

* cited by examiner

701A

701B

INHALATION DEVICE WITH CONSTRICTED FLOW PATHWAY

PRIORITY INFORMATION

This is a continuation application of U.S. patent application Ser. No. 16/249,477, filed Jan. 16, 2019, in the United States Patent and Trademark Office, which application claims priority from U.S. Provisional Application No. 62/585,565 filed Jan. 17, 2018 and U.S. Provisional Application No. 62/621,795 filed on Jan. 25, 2018, each filed at the U.S. Patent & Trademark Office, the disclosures of which are incorporated herein by reference in their entirety.

BACKGROUND

Field

This disclosure is directed towards inhaling devices, such as, vaporizers, vaporizing pens, and vaporizing machines, which are used to vaporize substances such as tobaccos, oils, liquids, medical drugs, and plant herbs. Once vaporized, these substances are then inhaled by consumers. Such inhaling devices have health benefits over traditional smoking methods. However, inhaling the vapor can have negative effects on the body depending on the substance, such as, nicotine. Inhaling devices have become more popular with consumers, but pose problems.

For example, while vaporizers can be safer than traditional smoking methods, it is difficult to meter the amount of vaporized substance that is being inhaled. So a user of an inhalation device that vaporizes nicotine may actually consume more nicotine than had the user smoked cigarettes or cigars.

There are multiple factors that affect the quantity of drug that is inhaled. These factors include the drug concentration of the vaporized substance, the amount of vapor inhaled, the duration of inhalation, variations between inhalation devices, and variation and inconsistency in the functionality of the device.

Another issue is that the inhaled substances may have different effects on different users depending on various factors. To optimize a user's experience, it is necessary to track the quantity inhaled taken over time and track the resulting effect it has on that user. This can be a tedious and demanding task. Typical users may not keep track of each dose and record the experience.

Known prior art such as U.S. Patent Publication No. 2005-0068528 (Altobelli) requires a pressure sensor to meter drug delivery. However, an additional pressure sensor adds cost and can complicate construction. Thus, a need exists in the conventional technology to provide an inhalation device that provides metering without a pressure sensor.

SUMMARY

According to an aspect of the disclosure, an inhalation device for providing metering information regarding vaporized substance inhalation to a user is disclosed. The inhalation device may comprise: a main body comprising a channel through which the vaporized substance can flow, the main body may include an inlet that is a first opening and an outlet that is a second opening. The inhalation device may also include a light source that emits light and that is positioned inside of the channel and a light sensor that senses an intensity of the light emitted from the light source. The inhalation device may also include a puff detecting element, a memory and a processor or circuit.

In an aspect of the disclosure, the processor or circuit may be configured to perform a metering method. The metering method may be performed when (in response to) a signal indicating that a puff has been detected by the puff detecting element. The metering method may include starting a heating element to begin vaporizing the substance. The metering method may also include extracting, from the memory, a predetermined known flow rate that is stored in the memory in advance, the predetermined known flow rate being a known flow rate of either the inhalation device itself or a portion of the channel of the inhalation device. The metering method may also include determining, based on the extracted known flow rate and information received from the light sensor regarding the intensity of the light emitted from the light source, an amount of vaporized substance that has been produced. The metering method may also include accumulating the determined amount of vaporized substance that has been produced in the memory as a total amount produced.

The metering method may also include a function such that when the accumulated total amount produced reaches a predetermined threshold dosage amount: (i) shut off the heating element or (ii) send a signal to an indicator or display that the predetermined threshold amount of the vaporized substance has been consumed.

According to another aspect of the disclosure, the light signal device and the sensor may be positioned in the channel such that the vaporized substance can flow past the light sensor and the light source. According to another aspect of the disclosure, the puff detecting element may include at least one of: a fin or propeller positioned in the vapor flow pathway to spin as the air/vapor passes, a heated wire positioned in the airflow pathway such that passing air will create a drop in the temperature of the wire, a temperature sensor located downstream from the heating element as to measure the temperature of the passing air, and a sensor positioned on the mouthpiece such that when the user's lips touch the mouthpiece, a puff is detected.

According to another aspect of the disclosure, the determining of the amount of vaporized substance includes: obtaining a predetermined number of readings from the sensor in a predetermined amount of time, determining a percentage, which is a vapor factor, as a ratio of an expected amount of production for the predetermined amount of time to the actual amount of vapor produced over the predetermined amount of time, multiplying the predetermined amount of time by the vapor factor at that time, and determining a total amount that has been consumed by accumulating each multiplication product.

According to another aspect of the disclosure, the processor or circuit may be further configured to: determine the amount of vaporized substance based on a correlation between a light intensity and a vapor/air mixture. According to another aspect of the disclosure, the correlation may be based on a graph of a value percent drop in light intensity versus a percentage of vapor in a mixture of vapor and air.

According to another aspect of the disclosure, the correlation may be based on a data structure or graph of a value percent drop in light intensity versus a percentage of cannabis oil vapor in a mixture of vapor and air.

According to another aspect of the disclosure, the processor or circuit uses data from the light sensor to meter the consumption of the vaporized substance, and/or the predetermined known flow rate that is stored in advance is based on a length of the second channel portion.

According to another aspect of the disclosure, the indicator informs the user when a dose of the substance has been inhaled, and the indicator includes at least one of: an audio signal, a visual signal, a visual display, a vibration and a transmitter that sends a signal to an external device.

According to another aspect of the disclosure, the inhalation device may further comprise an atomizer configured to vaporize an unvaporized substance into a vaporized substance.

According to another aspect of the disclosure, the first opening may be configured to allow entry of air into the device that flows to the atomizer such that the air flows at a substantially constant rate. According to another aspect of the disclosure the processor or circuit may use the substantially constant rate and the data from the light sensor to meter an amount of vapor consumed by a user. According to another aspect of the disclosure, the channel may include a first channel portion and a second channel portion, and when a user inhales, the vapor will flow in the first channel portion and through the second channel portion before flowing through the outlet. According to another aspect of the disclosure, the light source and the light sensor may be positioned for sensing concentration of the vapor that flows in the second channel portion.

According to another aspect of the disclosure, to perform the sensing of the concentration, the light source and the light sensor may be positioned such that they are attached at respective ends of the second channel portion. According to another aspect of the disclosure, the respective ends of the second channel portion may be parallel to each other and perpendicular to the vapor flow direction in the first channel portion.

According to another aspect of the disclosure, where the vapor flow direction in the first channel portion is an X-axis of a local coordinate grid, a ceiling of the second channel portion may be completely or partially below the first channel portion, where “below” means on a different, lower Y-coordinate plane of the local coordinate grid. According to another aspect of the disclosure, the second channel portion may be relatively provided at a level below the first channel portion. According to another aspect of the disclosure, the inhalation device may be configured to cause the vapor to: upon exiting the first channel portion, travel in a downward direction to and into the second channel portion, and/or upon exiting the second channel portion, travel in a direction upwards to the outlet.

In another aspect of the disclosure, the second channel portion may be completely or partially provided in a direction different from “below” the first channel portion. For example, the second channel portion may be provided “above,” “left of” and/or “right of” the first channel portion. When exiting the first and second channel portions, the vapor may travel upward, downward, leftwards, and/or rightwards so long as the vapor travels from the first channel portion to and through the second channel portion, and exits the second channel portion.

According to another aspect of the disclosure, the inlet may comprise a channel having at least two sidewalls, and the flow rate through the channel may be limited by surface tension and friction between the air and the sidewalls.

According to another aspect of the disclosure, the inhalation device may further include a plunger that is positioned at the inlet and is configured to move in an axial direction to limit airflow into the device.

According to another aspect of the disclosure, the processor or circuit may be further configured to at least one of: produce discreet pulses of vapor at a preset frequency and or produce vapor quantity in the pattern of a sine wave.

BRIEF DESCRIPTION OF THE DRAWINGS

Further features, the nature, and various advantages of the disclosed subject matter will be more apparent from the following detailed description and the accompanying drawings in which:

FIGS. 1A and 1B are each diagrams of an inhalation device, according to an embodiment of this disclosure.

FIG. 2 is another diagram of an inhalation device, according to an embodiment of this disclosure.

FIG. 3 is another diagram of an inhalation device, according to an embodiment of this disclosure.

FIG. 5 is another diagram of an inhalation device, according to an embodiment of this disclosure.

FIGS. 6A and 6B each show a diagram of a portion of an inhalation device, according to an embodiment of this disclosure.

FIGS. 7A-7D each show a diagram of a portion of an inhalation device, according to an embodiment of this disclosure.

FIG. 8 another diagram of an inhalation device, according to an embodiment of this disclosure.

FIG. 9 is a graph illustrating performance of an inhalation device according to an embodiment of this disclosure.

FIG. 10 is a diagram of a portion of an inhalation device, according to an embodiment of this disclosure.

FIGS. 11A-11C are diagrams of a portion of an inhalation device, according to various embodiment of this disclosure.

FIG. 12 is a graph illustrating performance of an inhalation device according to an embodiment of this disclosure.

FIG. 13 shows a graph of the value percent drop in an optocell (i.e., a device that senses the intensity of light) versus the percentage of vaporized drug in a mixture of vapor and air.

DETAILED DESCRIPTION

FIG. 1A is a cross-sectional view illustrating an inhalation device 1 according to an embodiment. Referring to FIG. 1A, the inhalation device 1 may include a battery 2, a heating element 4, a wick 6, a reservoir 8 containing a substance 10, a processor 14, a memory 16, a timer 18, a light emitter 20, which is a light source, a light receiver 22 (which may be or include a light sensor), a visual indicator 24, a quantity meter indicator 26, an inlet (e.g., two inlet holes 28), an outlet 30, and a main body 32.

The battery 2 provides electrical power to various components in the inhalation device 1, including the heating element 4, the processor 14, the memory 16, the timer 18, the light emitter 20, the light receiver 22, and the visual indicator 24. The battery 2 may be from among many different types (e.g., rechargeable batteries, etc.) as would be appreciated by an artisan having ordinary skill in the art.

The heating element 4 may be an element designed to heat up the wick 6 and thereby vaporize the substance 10. The heating element 4 may be made of many different types of materials, such as, metal, ceramics, glass, or a combination thereof. Additionally, the heating element 4 may be designed in many different shapes, such as a coil, a rod, etc. In the embodiment shown in FIG. 1A, the heating element 4 is exemplarily shown in a curved shape, but is not limited thereto.

The reservoir 8 is a housing that contains the substance 10. The reservoir 8 may be detachably attachable to the body 32 of the inhalation device 1 and may be implemented in many different configurations known to those skilled in the art, e.g., pods, cartridges, etc. Alternatively, the reservoir 8 simply may be an opening or cavity designed to receive the substance 10. The substance 10 may be many different types of smokable substances, such as tobaccos, oils, liquids, medical drugs, or plant herbs. The reservoir 8 stores the substance in unvaporized form, and the heating element 4 may heat the unvaporized substance from the reservoir 8 via the wick 6 to create a vaporized substance, which is then inhaled by the user through the outlet 30. The device 1 also includes a channel portion 40 through which the vaporized substance produced by the heating element 12 and air will flow to the outlet 30 when a user inhales (the airflow being represented by solid or broken arrows in the drawings).

The processor 14 is a hardware component (e.g., a hardware processor or hardware processing circuit) configured to control the operations of the other electrical components in the inhalation device 1. To achieve this, the processor 14 transmits and receives electrical signals to and from the other electrical components. The memory 16 may store detected pressure values and other types of information, e.g., battery information, programs, etc.

The timer 18 and processor 14 may work in conjunction to provide metering information to the user. More specifically, the processor 14 may control the timer 18 such that when a user inhales using the inhalation device 1, the processor 14 will start the timer 18 simultaneously (or within a predetermined time period) with the heating element 4 to begin vaporizing the substance 10. After the timer 18 has reached a particular value, a particular amount of the substance 10 will have been vaporized, and the timer 18 may shut off and send a signal to the indicator 24 to alert the user. Alternatively, the processor 14 may not shut off the heating element 4, but rather may send a signal to the indicator 24 that the particular amount of the vaporized element has been consumed.

The light emitter 20 (also referred to in this disclosure as light source and/or signal) may be configured to emit a wide range of light wavelengths. The light emitter 20 may be, for example, an LED, although is not limited thereto. The light emitter 220 emits the light towards the light receiver 22, and based on the received light from the light receiver 22, the processor can detect the concentration of vapor in the air and transmit an electrical signal indicating the detected concentration. This feature may be useful to assist a user in determining an amount of vaporized substance being consumed. The light emitter 20 and light sensor 22 may be implemented in many different configurations, may be spaced apart from each other in many different arrangements, and may use many different types of signals (e.g., visible light, ultraviolet, infrared, etc.). According to certain exemplary embodiments, the light emitter 20 and light receiver 22 may be omitted.

The visual indicator 24 may be a light that indicates that a certain event has occurred. For example, the indicator light 24 may light up when the processor 14 determines that a certain quantity of substance 10 has been consumed. The indicator light 24 is not limited to transmitting a light beam, and may instead generate many other types of indications, e.g., audio, another type of visual feedback, haptic (vibration) feedback, a display, etc. The device 1 could also, instead of an indicator 24, include a communication interface configured to transmit a signal to an external device such as a smart phone, tablet, or computer indicating that a dose has been consumed, when the certain quantity (dose) of substance has been consumed. Alternatively, the indicator 24 could display what dosage amount the user has consumed.

For example, for a particular amount that is set at 3 mg and for a heating element 212 that produces 1 mg of vapor per second, 3 mg will be delivered to a user who inhales for 3 seconds. In the event that the user cannot inhale long enough to consume a single dose in a single inhalation, the device 200 may be configured to keep a session open (via the memory and processor), with a session being defined as a particular time within which a user can consume the particular amount. A session in this case could be set to 10 seconds. In this open session configuration, the device 1 can stop producing vapor when the user stops inhaling and start producing vapor when the user inhales again. When the sum of the user's inhalations amounts to consumption of 3 mg, the processor may send a signal to the indicator 24.

Determining when the user stops inhaling can be achieved by using a pressure sensor. In this example, when the pressure drops below a threshold, the heating element will turn off, and when the pressure goes above the threshold, the heating will resume. Alternatively, instead of time-based, a session can be vapor-based, where the device 200 keeps a session open until a certain quantity of vapor is produced. As discussed more in regards to FIGS. 2-11 below, in an embodiment, a metering inhalation device that does not require a pressure sensor is disclosed.

The quantity meter 26, which is a progressive meter indicator, provides visual indicia that indicates a quantity of the substance 10 that been consumed. For example, the quantity meter 26 may include a series of hash marks oriented along an axis where the hash marks function as indicia of units of the substance 10 being consumed. According to exemplary embodiments, the hash marks may be evenly spaced apart from each other to indicate a cumulative increase in a quantity of the substance 10 being consumed. For example, each of the hash marks can represent 1 milligram (mg) of the active ingredient in substance 10. In an embodiment, the hash marks may also be unevenly spaced apart to account for resin buildup which increases the concentration of an active ingredient (e.g., THC) during smoking.

The quantity meter 26 could take the form of a sequence of lights, possibly LED lights, which indicate the progression of the amount consumed by the user. For example, as the quantity meter 26, there could be a sequence of four LED lights on the device 100 that indicate when 25%, ½, 75% and a full amount, respectively, have been taken. When the full amount has been taken, the lights might be programmed to indicate to the user that the full amount has been reached by flashing. Alternatively, the progressive meter indicator (quantity meter 226) could take other forms, like a mechanical indicator, a dial, a screen display, or a sound sequence. The progressive meter indicator may reset after reaching a full amount and hence continue to meter and indicate the user beyond one cycle. For example, after a full amount has been taken the indicator will reset by turning all lights off and begin turning on each light again as the user consumes.

The light source (signal or light emitter) 220 may be a light emitting diode (LED) that produces light in a wide range of light wavelengths. The signal could also be a light source that produces ultraviolet light. As shown in FIG. 1A, the light receiver or sensor 22 and light emitter 20 (or light signal) may be positioned across from each other in the channel. The light sensor 22 may sense the intensity of light, thereby allowing the processor to sense the concentration of the vapor. For example, the sensor 22 can be an optical sensor that senses the intensity of the light produced by the signal from light emitter 20. If the sensor 22 senses a high output, the processor can determine that this indicates that the vapor concentration is low, and the vapor/air mixture is mostly, if not all, air. If the sensor 22 senses a low output, the processor can determine that this indicates that the vapor concentration is high. The processor 14 may record information from the sensor 22 in the memory. The sensor 22 can assist the device 1 in providing information about vapor concentration to the user. For example, if the sensor senses a 5% drop in intensity from the signal, that could correlate to a mixture of vapor/air that is 60% vapor.

The processor 14 may use data from the sensor 22 to calculate when a particular amount of the vaporized substance has been produced. This is useful where the substance is viscous such as cannabis oil. In such viscous substances the amount of vapor produced in a given time can vary.

When a user inhales using the device 1, the processor 304 may turn on the heating element 4. The light receiving sensor 22 may sense in real time (as a non-limiting example, every 0.1 seconds) the intensity of the light from the signal 20. Using the data from the sensor 22, the processor 214 can determine when a particular amount of vapor has been produced (presumably consumed). For example, if the heating element produces 1 mg of vapor per second, and the particular amount is 3 mg, the processor may turn on the heating element 4 when a user inhales, and the processor may turn off the heating element 4 when the timer reaches three seconds. After the timer reaches 3 seconds, the processor may send a signal to the indicator 24, which will then indicate that the particular amount has been consumed.

For example, if a particular amount to be consumed is 3 mg and the heating element 4 vaporizes 1 mg per second (vaporization rate), then theoretically the 3 mg should be produced in 3 seconds. In practice, however, it may take longer for the inhalation 1 device to vaporize 3 mg. This may be due to factors such as the time it takes the heating element 4 to heat up and the consistency of the drug released from the reservoir 8 to the wick 6. So for example, when a user begins to inhale, the first ten readings of the sensor 22 in the first second (e.g., one reading every 0.1 seconds) may indicate that the vapor produced over the first second is 50% of the expected production. This percentage of expected production can be thought of as a vapor factor. The processor 214 may take this vapor factor into account to determine when 3 mg is consumed by the user. In other words, the processor 14 may collect the data from the sensor 16 at predetermined intervals (e.g., every 0.1 seconds) and, in view of the vapor factor, determine when 3 mg has been consumed by the user. For a given amount of time, the processor 214 may, for example, multiply the predetermined interval (e.g., 0.1 seconds) by the vapor factor for that predetermined time interval, for each of the intervals that have occurred, and add each of these products together to derive a total amount consumed. For example, if in the first second of inhalation, 50% of vapor is produced, and assuming 100% of vapor is produced after 1 second, the processor will able to determine that 3 mg has been consumed in 3.5 seconds.

In the above example, the processor 14 is capable of acquiring data from the light sensor 22 and also, from the memory, information on how much a particular amount of substance is expected to be produced per unit of time. The processor 14 can store additional vapor characteristics of the substance. For example, the processor 14 can store the time it takes for the heating element 4 to heat to the temperature at which it vaporizes the substance. The processor 14 can also store the heating and temperature variations during different inhalation profiles. For example, if a user inhales at a high rate, the air flowing through the inlet and into the device 1 can cool the heating element 4. The processor 14 can store, in the memory, information on different rates of inhalation to adjust, for example, the temperature of the heating element 4. The processor 14 can also store information on the flow of drug from the reservoir 8 to the wick 6, the concentration of the substance within a given volume, and the vaporization rates of the substance at different temperatures of the heating element 4. The processor 14 as well as the processors discussed herein can be standard integrated circuit (IC) chips made by IC manufacturers such as Texas Instruments, or a microprocessor.

Figure 3:
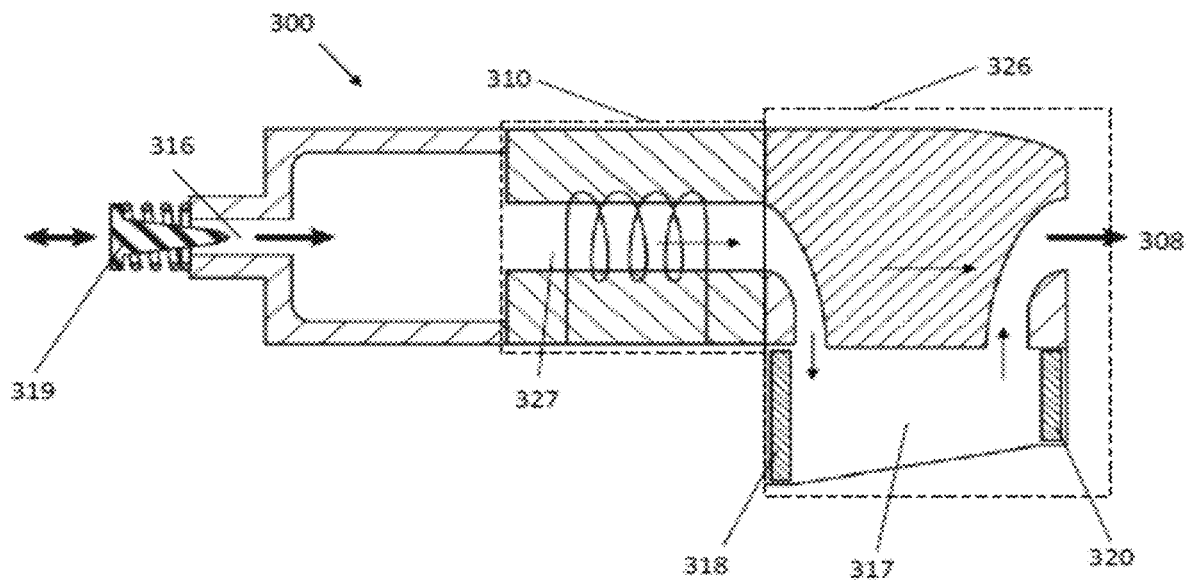
Figure 13:
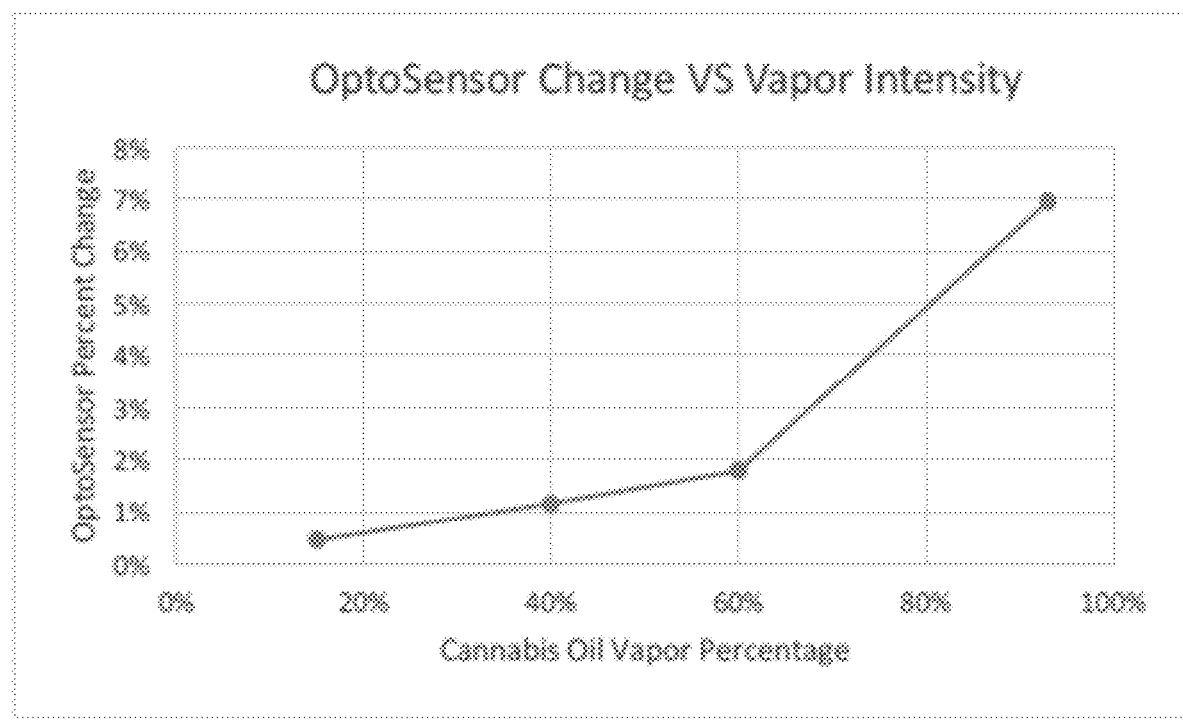

For example, data from the light receiving sensor 22 can assist the device 1 in providing information about vapor concentration to the user. For example, if the light sensor 22 senses a 5% drop in intensity from the signal from the light emitter 20, that could correlate to a mixture of vapor/air that is 60% vapor. The "OptoSensor Change v. Vapor Intensity" chart in FIG. 13 is an exemplary chart that graphs the value percent drop in an optocell (i.e., a device that senses the intensity of light) versus the percentage of cannabis oil vapor in a mixture of vapor and air. FIG. 3 thus shows a correlation between vapor concentration and the readings from an optocell. Knowing the relative concentration of the vapor can assist the device 1 in providing additional information to the user. For example, if a user inhales using the device 1 and the light receiving sensor 22 senses a high output, this may indicate that the concentration is less than expected. The device 1 could also include an additional indicator to inform the user that the device 1 is not producing the expected amount of vapor. The light receiving sensor 22 can be any suitable sensor that senses light including without limitation, a photosensor, photodetector, optocell, optoresistor, optotransistor, optodiode, and/or solar cell. The light emitter 20 can be any suitable device that produces light, such as an LED that produces visible light. The light source could also emit ultraviolet light. In other words, the light emitter 20 can produce a wide range of wavelengths of light and the light receiving sensor 22 can detect those wavelengths of light. The inhalation device 1 can optionally use filters in order to target a specific wavelength of light to optimally detect vapor intensity.

In addition, the light emitter 20 can also be tuned to particular wavelengths or a plurality of wavelengths to detect specific types of molecules and quantities of these molecules that are present in the passing vapor, thereby allowing identification and quantification of drugs in vaporized form. This technology can be fitted in a small and limited space such as a compact inhalation device 1. The vapor itself can remain in its current unaltered state during analysis. This technology allows for real-time analysis as it is being inhaled by the user. Several wavelengths of light may be used concurrently.

This technology can also be used for an exhalation device. In this configuration, we can analyze the air or vapor exhaled by a user. One such use of this configuration is to quantify the amount of drug that is being exhaled after partial absorption in the lungs. Another use of this configuration may be to make a determination on the level of drug within a human by way of analyzing the exhaled air/gas.

Although not required, in another embodiment, the device 1 may include a pressure sensor 12 that is designed to sense the air pressure in the vicinity of the outlet 30. According to an embodiment, the pressure sensor 12 is a sensor that can convert a detected pressure value into an electrical signal. The pressure sensor 12 may be implemented using many different types of pressure sensing technologies, such as micro air flow sensors, a propeller, a microphone, differential pressure sensors, strain gauges, fiber optics, mechanical deflection, semiconductor piezoresistive, microelectrical mechanical systems (MEMS), vibrating elements, variable capacitance, etc.

The pressure sensor 22 may be used to measure the velocity at which the mixture of vapor and air flow through the channel. So for example, if the pressure sensor 12 is a propeller, the propeller would be installed in the channel and would spin according to velocity of the vapor/air mixture. The frequency of revolutions can be measured and used to calculate the velocity of the mixture. If the pressure sensor 12 is a microphone, the microphone can be set up in the channel to listen to the noise of the vapor/air mixture passing through the channel. A correlation can be made between the sound intensity (and/or frequency) and the rate of flow of the mixture. Optionally, the sensor 12 can be placed between the inlet and the processor such that it detects the air flow rate going through the device when a user inhales. Generally, the vapor light sensor and airflow rate are needed in order to properly derive the mass flow rate of the medication. The vapor light sensor may provide light intensity data, which be used to determine density data, and the airflow rate will provide data regarding the speed of inhalation (i.e.: how much of the vapor density is being consumed). There are several improvements related to this section. They are further described in the embodiments below.

In general, when a user ignites the substance 210 and inhales through the outlet 30, air from outside is drawn into the inlet 28, moved through the body 32 of the inhalation device 1 and mixed with the vaporized substance, and pulled through the outlet 30 into the user's lungs. During this process, the air in the area around the outlet 30 flows towards the low air pressure (e.g., vacuum) created by the user inhaling the air. A greater change in air pressure results in a greater quantity of vaporized substance being consumed by the user. When the pressure sensor 12 is implemented as a differential pressure sensor, the pressure sensor 12 detects this change in air pressure, converts the detected values to an electrical signal, and transmits the electrical signal to the processor 14. According to an embodiment, since the pressure sensor 12 is designed to be used in a small portable device (i.e., the inhalation device 200), the pressure sensor 12 may be designed as a relatively small and highly sensitive micro air pressure sensor that is capable of detecting tiny changes in air pressure (e.g., a fraction of a pascal), although is not limited thereto.

The pressure sensor 12 can also be used to adjust the intensity of the heating element 4. The temperature of the heating element can affect the amount of the substance that is vaporized. The sensor 12 is able to sense how intensely a user inhales (i.e., senses the volume per unit time of an inhalation). The processor 14 can acquire this data and adjust the intensity of the heating element by adjusting the voltage of the heating element.

The pressure sensor 12 and the adjustment of the heating element 4 are useful in a non-limiting situation where the user desires to consume a dose more quickly. So, for example, if the device 1 is set up so that the heating element 4 produces 1 mg of vapor per second and a dose is 3 mg, a user that inhales at a high volume per unit time can consume the entire dose quicker than 3 seconds. In this scenario, the pressure or airflow sensor 12 will be able to sense the higher velocity of the vapor/air mixture, and the processor can, if desired, increase the intensity of the heating element 4 such that it produces more vapor. The processor 14 can adjust the intensity of the heating element 4 in real time based on data from the air flow sensor 12. So if a user does not inhale intensely, the sensor 12 will detect the decreased flow rate and the processor can then lower the intensity of the heating element 4.

Figure 1B:
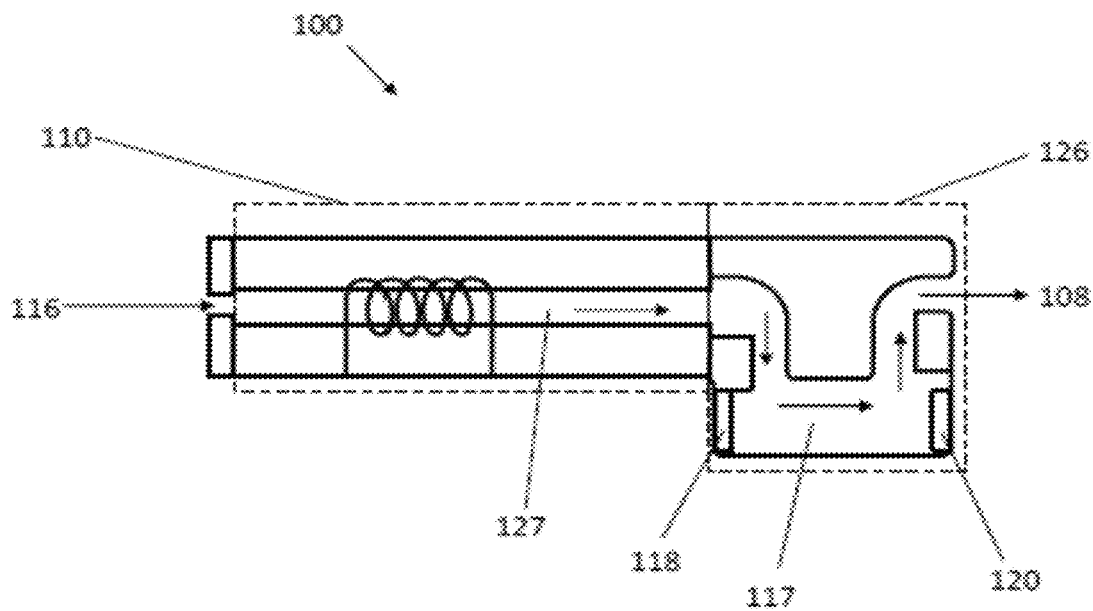

The embodiments described in FIG. 1B disclose an inhalation device that meter consumption of the vapor by use of a single sensor (the light sensor), but do not require the use of a pressure sensor. In other words, without the need for a separate airflow sensor. For example, FIG. 1B illustrates an inhalation device 100 according to an embodiment of this disclosure that may restrict the amount of air (or vapor/air mixture) that can be contained within one or more channel portions. More specifically, as shown in FIG. 1B, inhalation device 100 may include an inlet 116, an atomizer portion 110 (including an atomizer shown by coils in FIG. 1B), a vapor sensing unit 126 and an outlet 108. The atomizer portion 110 may include a first channel portion 127 and the vapor sensing unit 126 may include a light source (signal) 118, a light sensor 120, and a second channel portion 117. The atomizer portion 110 includes an atomizer that produces vapor that a user inhales through the outlet 108. When a user inhales, the vapor will flow in the first channel portion 127 of the atomizer portion 110 and through the second channel portion 117 of the vapor sensing unit 126 before flowing through the outlet 108. The light source (signal) 118 and light sensor 120 may be positioned for sensing concentration of the vapor that flows in the second channel portion 117, which is described in more detail below. To perform the sensing of the concentration, the light source 118 and the light sensor 120 may be positioned such that they are attached at respective ends of the second channel portion 117.

As shown in FIG. 1B, in another embodiment an inhalation device that meters consumption can be constructed without an airflow or pressure sensor. For example, a standard atomizer unit will produce vapor in varying degrees. This can be measured by a vapor sensing unit (e.g., the portion of the inhalation device that senses vapor concentration). As described in previous embodiments herein, a sensor for measurement of volume of flow can be used to measure the instantaneous flow rate. This data may be combined with vapor intensity readings in order to derive a mass flow rate of vapor and/or substance. This is accurate and true for systems in which the air flow rates may be variable. However, if the airflow rate is restricted to a substantially set (limited) rate, then there will be no substantial variation in flow rate. In such a case, the flow rate is set and there is no need to measure the pressure/air flow during that time for deriving the flow rate. The mass flow rate can be derived solely on the known flow rate and the vapor intensity (vapor density).

As shown in FIG. 1B, the respective ends of the second channel portion 117 may be parallel to each other and/or perpendicular to the vapor flow direction in the first channel portion 127. As shown in FIG. 1B, where the vapor flow direction in the first channel portion 127 is an X-axis of a local coordinate grid, a top (ceiling) of the second channel portion 117 may be completely (or partially) below the first channel portion 127, where below means on a different Y-coordinate plane of the local coordinate grid that has the X-axis corresponding to the vapor flow direction in the first channel portion 127. That is, as shown in FIG. 1B, the second channel portion 117 is provided at a level below the first channel portion 127. As shown in FIG. 1B, the inhalation device 100 may further be configured to cause the vapor to, upon exiting the first channel portion 127, travel in a downward direction that is perpendicular to the airflow direction of the first channel portion 127 and into the second channel portion 117. Upon exiting the second channel portion 117, the vapor may travel in a direction upwards that is perpendicular to the second channel portion 117. In a perpendicular direction may include precisely perpendicular and also substantially perpendicular.

However, the second channel portion may be completely or partially provided in a direction different from "below" the first channel portion. For example, the second channel portion may be provided "above," "left of" and/or "right of" the first channel portion. When exiting the first and second channel portions, the vapor may travel upward, downward, leftwards, and/or rightwards so long as the vapor travels from the first channel portion to and through the second channel portion, and exits the second channel portion.

While the light source 118 and the light sensor 120 allow a processor (or processing circuit) to determine vapor concentration, determining the volume of the vapor is needed to ultimately meter the quantity of drug consumed by a user. Conventionally, a second sensor (e.g., a pressure or airflow sensor) for measurement of volume of flow would be needed to measure a flow rate of the vapor. This second sensor data of the flow rate would be combined with a vapor concentration to derive a mass flow rate of vapor and/or substance. A person having ordinary skill in the art would understand that an atomizer produces vapor at varying degrees, and a user may inhale at varying intensities leading to a variable flow rate through a typical inhalation device. Thus, in conventional technology, having the second sensor (e.g., an airflow sensor to sense this variable data) would typically be required.

However, in the inhalation device FIG. 1B, the airflow rate is restricted to a substantially set (limited) rate. As a result, there is no need to measure the air flow with a separate second sensor. The mass flow rate can be derived based on, for example, a known flow rate of a specific channel portion in the device 100 and the vapor concentration. Alternatively, the known flow rate can be a known flow rate of the entire device itself.

In an embodiment, as shown in FIG. 1B, the vapor light sensor can be set up such that the air/vapor flow will pass substantially within "view" of the vapor light sensor. The flow pathway within the second channel portion 117 may be designed such that all the air/vapor is substantially visible to the vapor sensing unit. The design may include a pathway corresponding to the second channel portion 117 with at least one cross section that is entirely within view, within detection, of the vapor sensing unit. In this set up, substantially all the air/vapor will be forced to pass through this cross sectional area and thus will be visible and detectable to the vapor sensing unit.

There may be no hidden pathways or "corner" in which the vapor can pass without being detected by the vapor sensing unit. This embodiments advantageous as it measures substantially all air/vapor flowing within the unit and will result in accurate measurements and final calculation. The frequency of measurements by the vapor sensing unit will need to meet or exceed the airflow rate such that no vapor passes without being measured.

Specifically, and still referring to FIG. 1B, limiting the flow rate to a substantially particular rate can be achieved through physical design of the air and/or vapor flow pathway (referred to as channel portion(s)). For instance, in FIG. 1B, the inlet 116 can be of a specific diameter that may constrain the air flow to a substantially set/limited flow rate, which can be used for determining the known flow rate of the device.

As shown in FIG. 1B, the diameter of the inlet 116 is reduced to a small magnitude, for example around 1 mm in diameter essentially obtain a constant flow of air into the inhalation device from the inlet 116. This information can be stored, along with correlation information, which can be used to determine a flow rate of the inhalation device 100 or a portion thereof.

Figure 2:
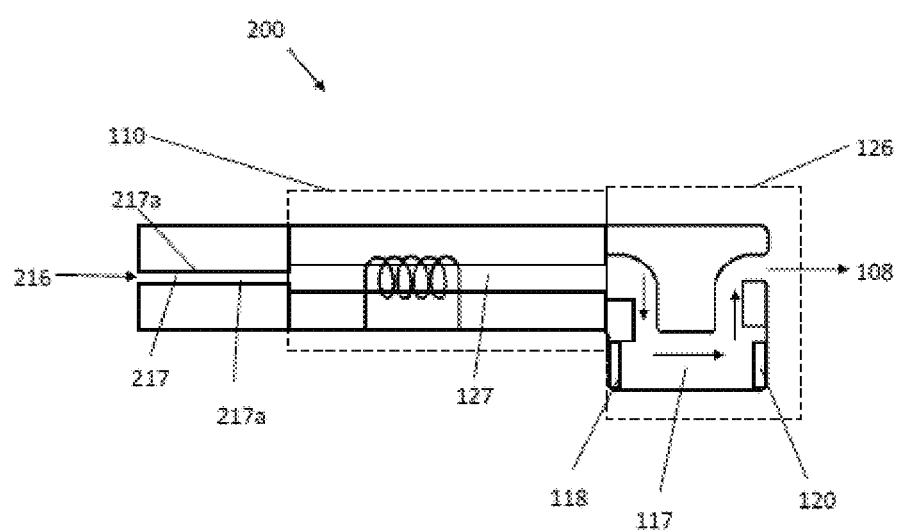

Alternatively, the inlet of an inhalation device can also be elongated to maintain a constant air flow. This is illustrated in FIG. 2, which shows inhalation device 200 according to another embodiment of the disclosure. FIG. 2 may include each of the elements of FIG. 1B with an exception being that an inlet 216 of FIG. 2 is longer than the inlet 116 of FIG. 1B, and comprises a third channel portion 217. The third channel portion 217 may have a smaller diameter than the first channel portion 127, thereby the third channel portion 217 may be used to control and limit the air flow rate through this channel by surface tension and friction between the air and the sidewalls 217a of the third channel portion 217. In an embodiment, the diameter of the hole maybe around 1 mm and the length approximately from 5-10 mm. The diameter of the hole that may be around 1 mm may be less than 1 mm or more than 1 mm. The diameter of the hole may be less than 2 mm, but greater than 1 mm.

FIG. 3 illustrates an inhalation device 300 according to another embodiment of the disclosure. More specifically, inhalation device 300 may include an inlet 316, an atomizer 310, a vapor sensing unit 326 and an outlet 308, which perform similar functions as the inhalation devices 100 and 200 described above. The atomizer 310 may include a first channel portion 327 and the vapor sensing unit 326 may include a light source or signal 318, a light sensor 320, and a second channel portion 317. The atomizer portion 310 includes an atomizer (shown by coils in FIG. 3) that produces vapor that a user inhales through the outlet 308. The vapor will flow in the first channel portion 327 of the atomizer portion 310 and through the second channel portion 317 of the vapor sensing unit 326 before flowing through the outlet 308. The light source 318 and light sensor 320 are positioned for sensing concentration of the vapor that flows in the second channel portion 317. The light source 318 and the light sensor 320 may be positioned on ends of the second channel portion 317.

As shown in FIG. 3, the inhalation device 300 may also include a plunger 319. The plunger 319 can move in an axial direction into and out of the inlet 316 and may be shaped like a coned needle that penetrates the inlet 316. The plunger 319 may be biased away from the inlet 316 such that the higher the air flow rate (i.e., the more intensely a user inhales), the more the plunger 319 gets "sucked in" to the hole and restricts the air flow rate. The plunger 319 can thus be used to restrict the air flow rate to a substantially set flow rate regardless of the intensity with which a user inhales.

Figure 4:
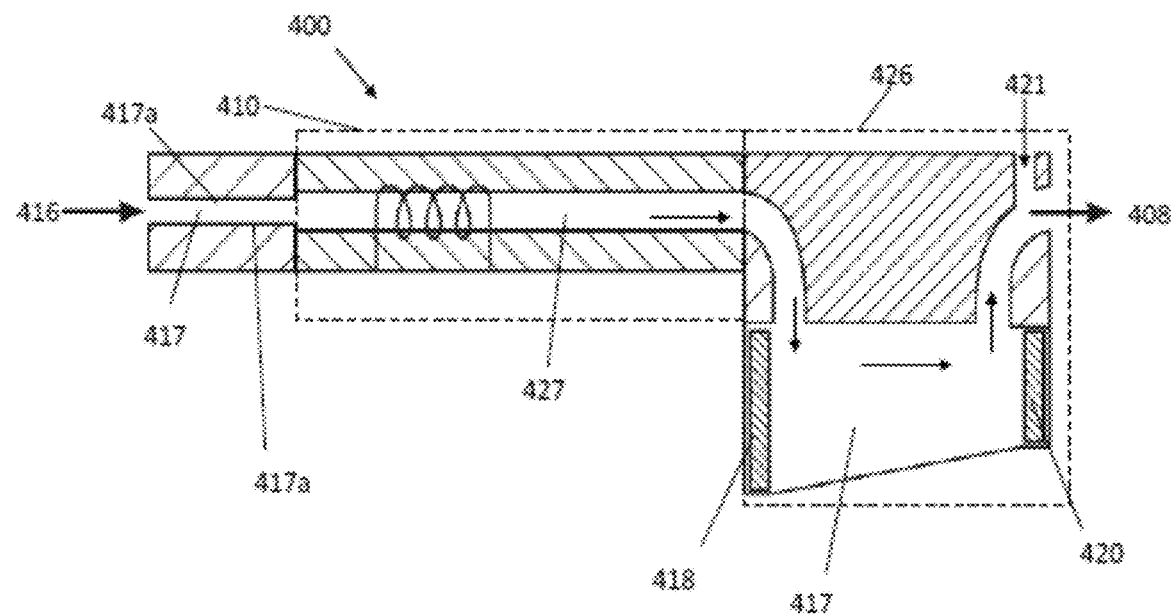

FIG. 4 illustrates an inhalation device 400 according to another embodiment of the disclosure. More specifically, as shown in FIG. 4, inhalation device 400 may include an inlet 416, an atomizer portion 410, a vapor sensing unit 426 and an outlet 408. The atomizer portion 410 may include a first channel portion 427 and the vapor sensing unit 426 may include a light source 418 and a light sensor 420 that are positioned within a second channel portion 417. The atomizer portion 410 may include an atomizer (shown by coils in FIG. 4) that produces vapor that a user inhales through the outlet 408. The vapor will flow in the first channel portion 427 of the atomizer portion 410 and through the second channel portion 417 of the vapor sensing unit 426 before flowing through the outlet 408. The light source 418 and light sensor 420 may be positioned for sensing concentration of the vapor that flows in the second channel portion 417. The light source 418 and light sensor 420 may be positioned on ends of the channel 417. The inlet 416 of the device 400 may be elongated and comprise a third channel denoted by sidewalls 417*a*. The third channel may be used to control and limit the air flow rate through this channel by surface tension and friction between the air and the sidewalls 417*a* of the third channel. To allow a user to inhale faster, while controlling the airflow rate in the atomizer portion 410 and/or the vapor sensing unit 426, the device 400 may include a second air inlet 421 that is separated from the airflow of the atomizer portion 410 and the vapor sensing unit 426. The second inlet 421 allows a user the freedom to experience a varying airflow rate, while maintaining a known airflow rate in the second channel portion 417.

Figure 5:
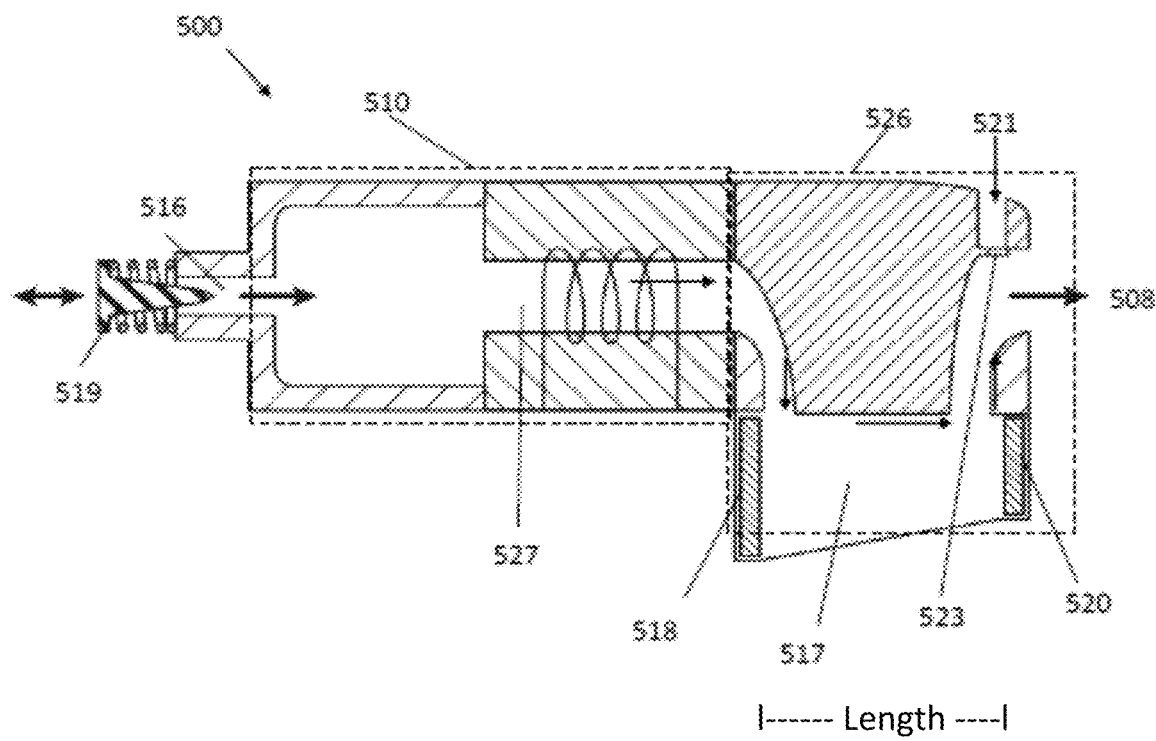

FIG. 5 illustrates an inhalation device 500 according to another embodiment of the disclosure. More specifically, inhalation device 500 may include an inlet 516, an atomizer portion 510, a vapor sensing unit 526 and an outlet 508. The atomizer portion 510 may include a first channel portion 527 and the vapor sensing unit 526 may include a light source 518, a sensor 520, and a second channel portion 517. The atomizer portion 510 includes an atomizer (shown by coils in FIG. 5) that produces vapor that a user inhales through the outlet 508. The vapor will flow in the first channel portion 527 of the atomizer portion 510 and through the second channel portion 517 of the vapor sensing unit 526 before flowing through the outlet 508. The light source 518 and light sensor 520 may be positioned for sensing concentration of the vapor that flows in the second channel portion 517. The light source 518 and the light sensor 520 may be positioned on ends of the second channel portion 517. The inhalation device 500 may also include a plunger 519 that operates as described with respect to plunger 319. In addition, the device 500 may include a second inlet 521 having an airflow valve 523. In this embodiment, the valve 523 of the second inlet 521 may be biased in the closed position and open after a certain airflow rate threshold is reached inside the device 500, thereby ensuring that air will first enter via the inlet 516 to the atomizer 510 and vapor sensing unit 526. Only after a certain airflow is reached, will the second inlet 521 be open. A threshold could be set around 20 ml/sec, so when a faster rate is presented by the user, it will open the second inlet hole and air will come in from there, thereby resulting in a consistent airflow rate in the first inlet hole and along the atomizer portion 510.

In another aspect of the present disclosure, controlling the airflow rate of an inhalation device can be derived without substantially restricting the airflow rate and without a sensor for measuring data relating to air flow rate. This embodiment is characterized in that variations in the vapor production essentially match variations in the airflow rate. So if the airflow rate increases by 50%, then the vapor production rate needs to increase by approximately 50%. In this embodiment, the light sensor (as described in various embodiments herein) can be used by the processor to identify increases in vapor density and account accordingly. Implementation of this embodiment can be achieved by design considerations to the location where the vapor is being produced, e.g., the atomizer portion of embodiments described herein. For example, the specific area of vaporization (where the liquid vaporizes) can be designed in such a way that this space may become saturated with vapor at a certain point.

Figure 6A:
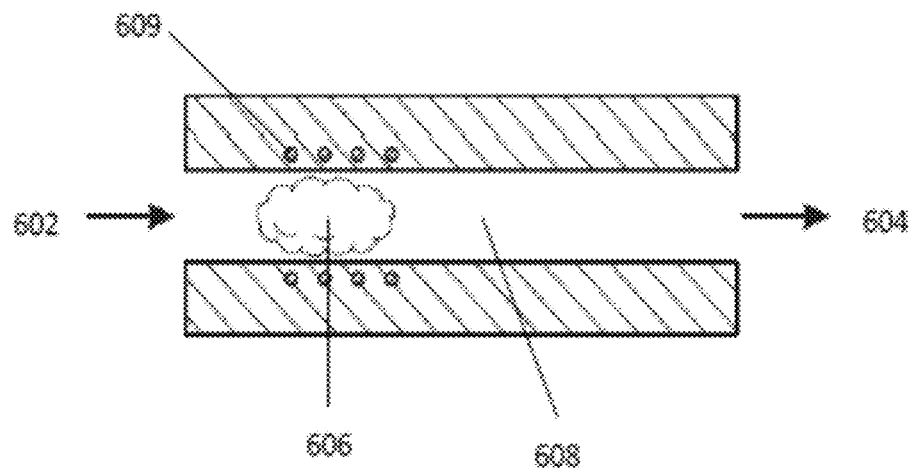

For example, FIG. 6A shows vapor saturation 606 created by heating element 609 in a vaporization area 608, which could correspond to a first channel portion described in FIGS. 1-5. As the air flows past this area (illustrated by the arrow from the inlet 602 through to the outlet 604), it will carry the vapor and provide un-saturated air to that space, which will in-turn get saturated, and so on. The slower the air moves, the less vapor is created per unit of time. The faster the air moves, the more vapor is produced per unit of time.

Figure 6B:
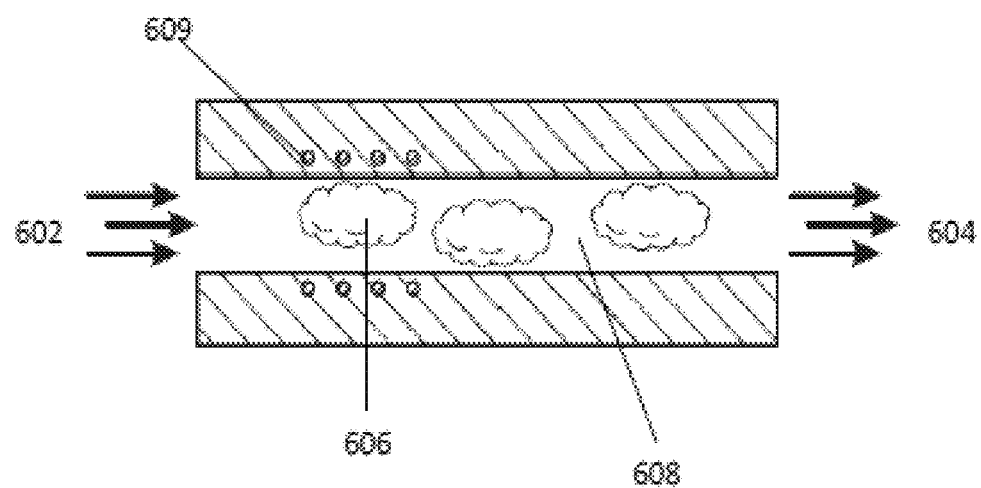

For example, FIG. 6B shows air flowing more quickly through the vaporization area and moving the vapor with it and allowing more vapor to be produced. In the embodiments shown in FIGS. 6A and 6B, the inhalation rate is not known. However, the increases and decreases in vapor density are measured by the vapor sensing unit as described herein and are accounted for by the microprocessor. Considering that a human has a limited range of inhalation rates, the embodiments described in FIGS. 6A and 6B can provide substantially accurate results.

In another embodiment, substantially accurate results as to determining airflow rate for an inhalation device may be derived without substantially restricting the airflow rate and without a sensor for measuring data relating to air flow rate and without a vapor sensor. This embodiment may be characterized in that the vapor production needs to be consistent with respect to time. For example, if the vaporization unit produced a set amount of vapor per second, for example, 1 mg/second, then the total amount of drug can be calculated based on the duration of a puff alone. In such a set-up, the production of vapor would need to be independent of uncontrolled variables such as air flow rates.

Figure 7A:
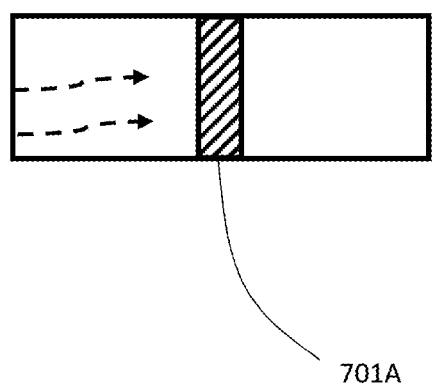

For example, in an embodiment shown in FIG. 7A, the inhalation devices described herein may include a puff sensor to detect the start and stop of a user's puff. This may include a puff switch that detects a pressure drop somewhere in the flow pathway. Various embodiments of puff sensors and/or airflow sensors can be implemented in an inhalation device as described herein. In one example, as shown in FIG. 7A, a fin 701A can be positioned in the airflow pathway such that the airflow (represented by solid or broken arrows in the drawings) will affect the fin 701 (such as by vibrating the fin 701A or by forcing the fin 701A in a direction). The fin 701A vibrations may be measured and a corresponding airflow rate determined based on a correlation derived by previous and simple experimentation. The fin 701A may also be positioned as to bend, turn, compress or stretch.

This motion may be measured and a corresponding airflow rate determined based on a correlation derived by previous and simple experimentation. The motion of the fin 701A may be measured by various means such as optical sensors, rotational motion sensors, resistance measurements, piezoelectric sensors and/or capacitance change created by the motion of the fin 701A on a capacitance sensor.

The fin 701A may be shaped as a propeller and positioned in the airflow/vapor flow pathway to spin as the air/vapor passes. The speed of rotation may be measured and an airflow speed derived by calculation or by previous and simple experimentation. These embodiments of FIG. 7A may be used as a puff detector/switch (to detect the start and stop of a puff) or to measure airflow rates.

Figure 7B:
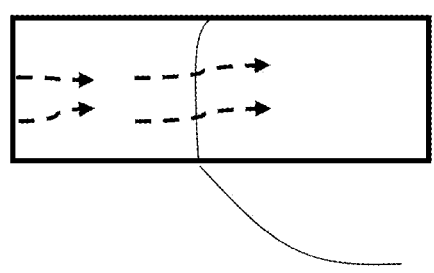

As shown in FIG. 7B, another embodiment includes having a heated wire positioned in the airflow (represented by solid or broken arrows in the drawings) such that the passing air will create a drop in the temperature of the wire 701B. The faster the flow, the more the temperature will drop. The temperature may be measured in real time and a correlating airflow rate may be determined by mathematical calculations or by a look up table. The look up table may be generated beforehand by simple experimentation of airflow vs temperature in this set up. This embodiment of FIG. 7B may be used as a puff detector/switch (to detect the start and stop of a puff) or to measure airflow rates.

Figure 7C:
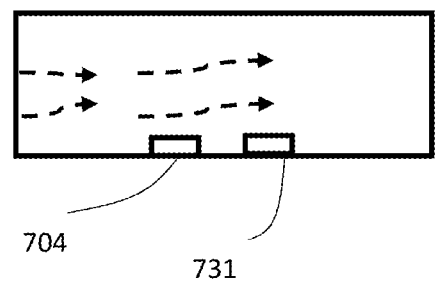

As shown in FIG. 7C, another embodiment may include the heated element 704 located in the air flow path. The heating element 704 may be heated to a specific temperature by the processor (or processing circuit). As shown in FIG. 7C, a temperature sensor 731 may be located downstream from the heated element as to measure the temperature of the passing air. The passing air will be heated by the heating element and then the temperature sensor will measure the temperature of that air. Different air flow rates will result in different temperature readings. In this embodiment, the heating element could be located within the airflow pathway. The passing airflow will create changes in temperature in said element. These changes in temperature may create variations in the current drawn by said element, and or variations in the resistance across said element. These variations in current/resistance may be measured. The airflow speed may be derived from these measurements by calculations or by previous experimentation. The FIG. 7C embodiment may be used as a puff detector/switch (to detect the start and stop of a puff) or to measure airflow rates.

Figure 7D:
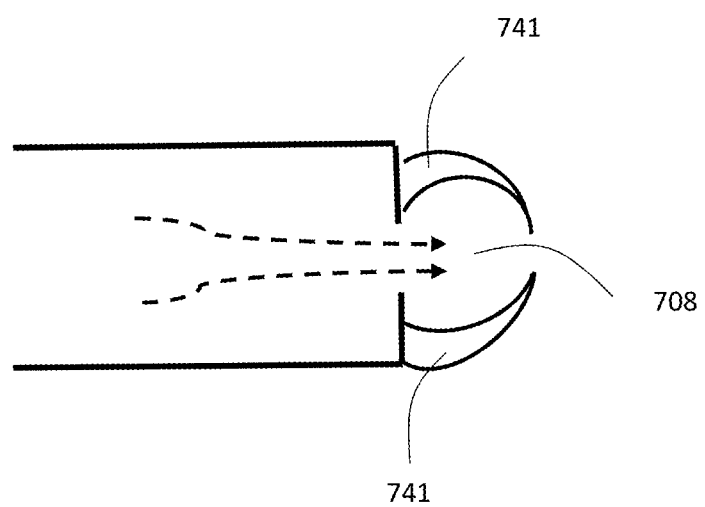

In another embodiment an inhalation device according to this disclosure may use a sensor positioned on the mouthpiece such that when the user's lips touch the mouthpiece, the sensor can detect this action. Preferably, as shown in FIG. 7D, a set of sensors 741 may be positioned in an outlet 708 such that the one sensor touches the top lip and the other the bottom lip. Capacitive and resistive touch sensors 741 may be used for the FIG. 7D embodiment. The above described embodiments may also be fitted with a push button that can be used by the user to initiate and/or activate the device. When the user stops pushing the button, the device can stop. In yet another embodiment, an inhalation device according to this disclosure may be configured in such a way that the user may define when the device will turn off. The user can define this by setting an amount of drug (dose) that they want to consume. The unit may remain operational until the dose is fully consumed. The device will measure the amount inhaled in real-time and will discontinue supplying vapor once the dose is met. This allows the user to get the dose that they want without actively monitoring the metering interface.

In another embodiment, the flow rate of the vapor by use of the vapor sensing unit may be determined in a different manner. For example, the vapor sensing unit may be set up in a way as to provide a pattern (or rhythm) to the vapor production. For example, the production of the vapor may be pulsed (on-off) at a known certain frequency, as shown in FIG. 8.

Figure 8:
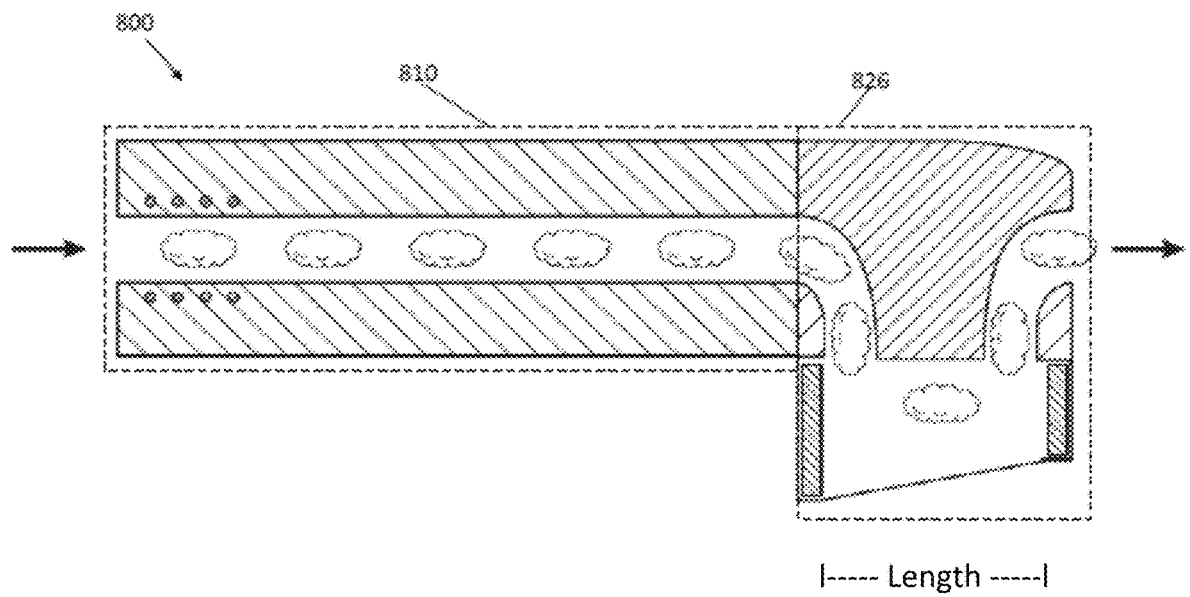
Figure 9:
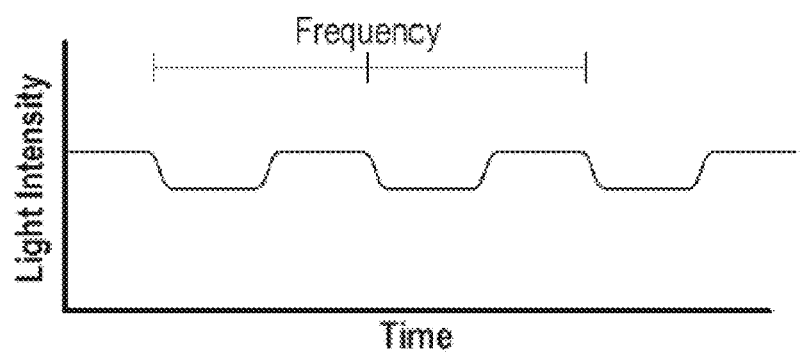

FIG. 8 shows an inhalation device 800 that includes an atomizer portion 810 and a vapor sensing unit 826 as described in various embodiments herein. The vapor sensing unit would identify these pulses in vapor production as increases and decreases in vapor density. By comparing the frequency of the identified pulses to the known frequency of vapor production, the flow rate of the vapor can be determined as shown in FIG. 9. This may be determined by calculation or by experimentation. In parallel, the density of the vapor can be determined by the intensity of the light for each pulse. This method would not be limited to on-off pulses. For example, a sine wave pattern may be chosen.

Vapor/air mixtures tend to be non-homogenous and poorly mixed. The density of the vapor may vary greatly within small distances. The density of the vapor may also change quickly depending on temperature, pressure, motion and turbulence. One can anticipate that measuring substantially all the air/vapor will yield better results than measuring only a portion of the air/vapor. When measuring vapor it is important to measure the vapor density often enough to properly characterize the vapor quantity. In a flowing environment, one may find snapshots of high density followed by low density. Ideally, the frequency of the snapshots would match the flow speed in such a way that all the vapor cross sections are captured. Such a set up may require that the snapshot frequency vary according to the flow rate. As an example in FIG. 8, the vapor will travel a length L in a certain amount of time dependent on flow rate. For example, the certain amount of time may be 0.25 seconds. In such a case, it would be advantageous to take a snapshot at least once per every 0.25 seconds to ensure all vapor is seen by the sensor. It may also be found that substantially good characterization of the flow is possible with less frequent snapshots. Such a determination can be made after proper consideration to liquid characteristics, physical pathway constraints and dynamics, temperature, desired level of accuracy and various other factors.

In yet another embodiment is an inhalation device, with metering capabilities as described in this disclosure, where the vapor is produced by vibrations (rather than heat). Such a device would have a reservoir for holding the drug in liquid form (could also be in solid form), and creating a vibration of certain frequency in order to transform the liquid into a vapor. A piezoelectric may be used to create the vibrations. The liquid may be held/suspended in a membrane that has small holes. The membrane may be metal and have porous qualities. The vapor produced may then be inhaled by the user. Adding heat to the vaporization method may help the performance of this device. Further, it may help create vapor particle sizes that are better suited for inhalation and absorption by the lungs. Particle size has an effect on how far into the lungs the particles may travel, thus affecting where the particles settle and may get absorbed.

In yet another embodiment is an inhalation device, with metering capabilities as described in this disclosure, for use with plants and herbs (or other naturally occurring materials). This device would include a heating element, a location or chamber to hold the plant material, a vapor sensor for measuring the vapor, it may have a pressure or airflow sensor for determining air flow speed. It may have a puff switch for detecting a puff. The puff switch or puff detector may be as described above.

In another embodiment is an inhalation device metering ability for 'dabbing'. This embodiment includes an inhalation device with metering, as described in this disclosure, for use with highly concentrated extracts. These extract may be solid or waxy. They may be substantially solid and non-fluid. This device would include a heating element, a location or chamber to hold substantially solid material, a vapor sensor for measuring the vapor, it may have a pressure or airflow sensor for determining air flow speed. It may have a puff switch for detecting a puff.

Figure 11A:
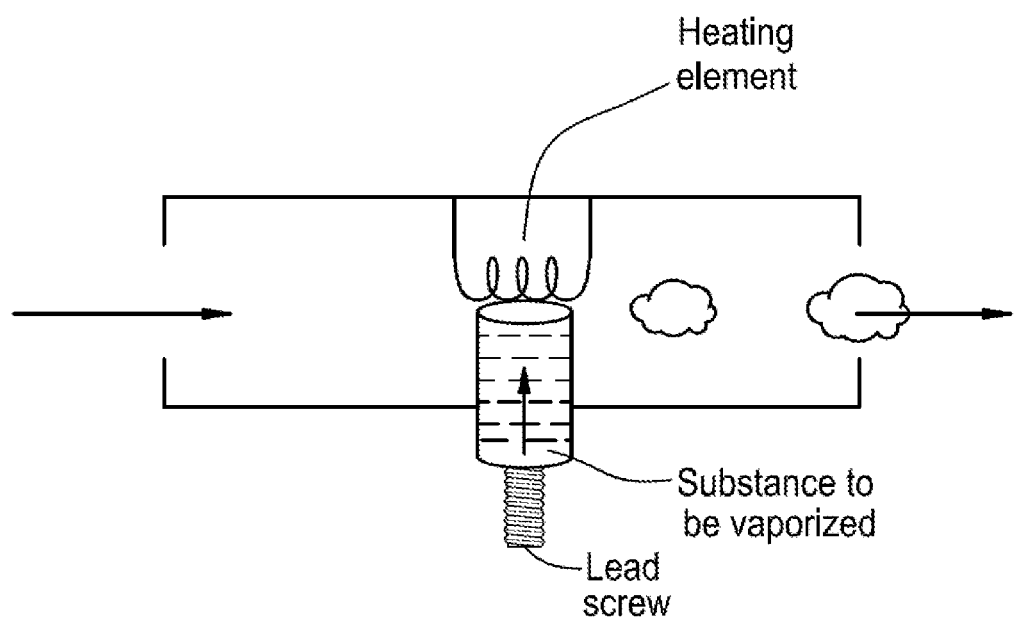

In embodiments described above, vapor is metered after it is produced. In another embodiment the material/drug is metered before it is vaporized (or as it is being vaporized). This embodiment requires metering the drug in to the vaporizing unit such that the amount that is being vapor is controlled by the metering process. For example, as shown in FIG. 11A, the drug may be made into a solid and fed into the heating element by a lead screw. The feed rate could be controlled and metered. The FIG. 11A embodiment could alternatively work with a liquid that is fed at a certain rate into a heating element for evaporation.

Figure 11B:
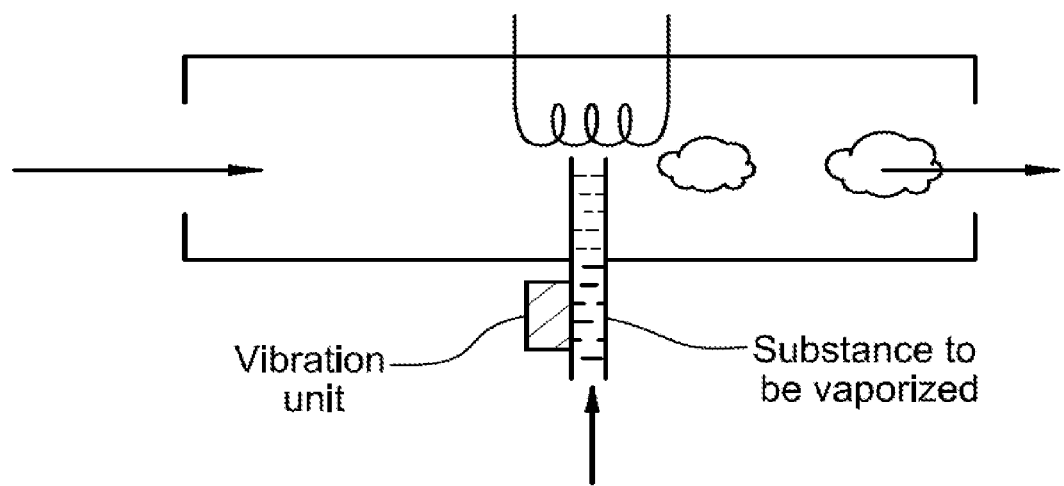
Figure 11C:
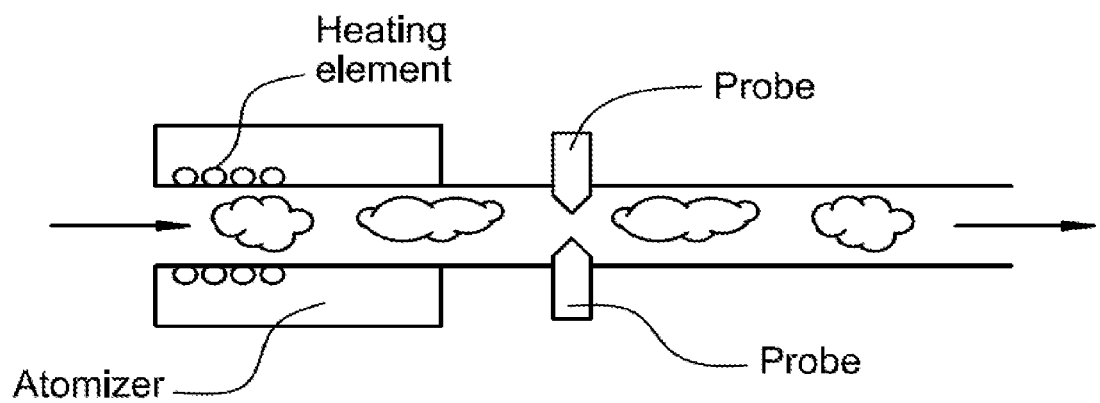

Another embodiment includes a piezoelectric/vibration unit to be used in a mechanical way to feed the drug into a heating element. In this embodiment, the drug can be situated in such a way that it can only move into the heating element. This can be achieved by a ratchet design or one way values that only allow motion in one direction. The vibration caused by the piezoelectric/vibrator can be set up in such a way that it will bias the drug into the heating element when activated. FIG. 11B illustrates an embodiment with this type of set-up. Another way is to feed the drug into the heating element by discrete individual touches (e.g., by touching the drug to the heating element for a certain amount of time and pressure). It may be necessary to repeat this action with high frequency to get the desired amount.

Figure 12:
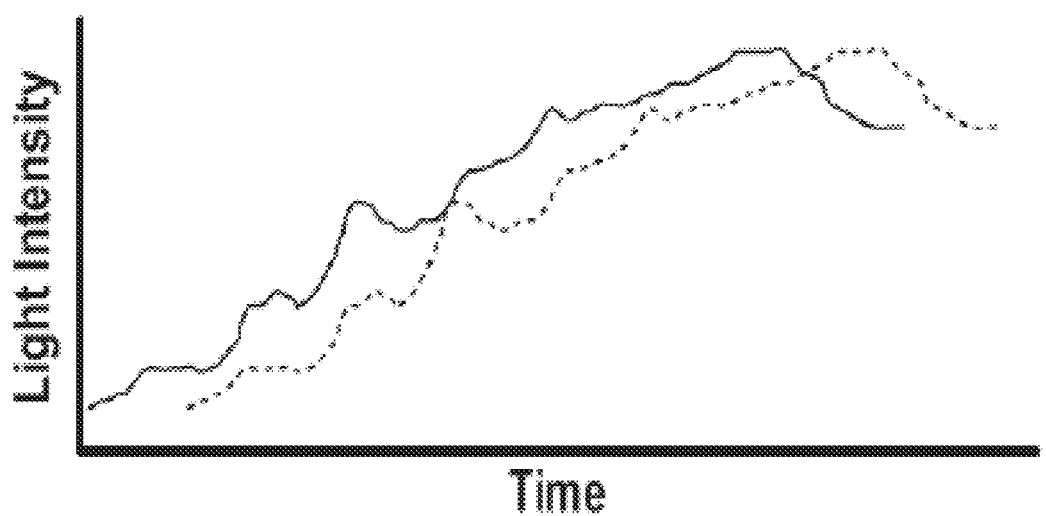

As shown in FIG. 12, another embodiment provides an alternative way to meter vapor in an inhalation device. More specifically, the FIG. 12A embodiment discusses a way by which to measure that density of vapor in a pathway. There would be two probes positioned in the vapor pathway. The probes would be located at a set distance from one another. The probes may be made of a conductive material. There could be a certain high amount of electrical resistance between the tips of the probes in the default "no vapor" state. This resistance could be measured and used as a baseline resistance value. As vapor flows past the probes, it will fill the space between the probes with particles of vapor. The vapor particles are more electronically conductive than air. Hence, the vapor will change the resistance reading between the probes.

The FIG. 12A embodiment may include that the resistance readings are amplified by changing the shape and orientation of the probes. Heat or an electrical charge may also improve the results. Another embodiment may include connecting the probes by a thin wire that is positioned to accumulate tiny particles of the passing vapor during flow. The resistance of the wire will change accordingly.

Figure 10:
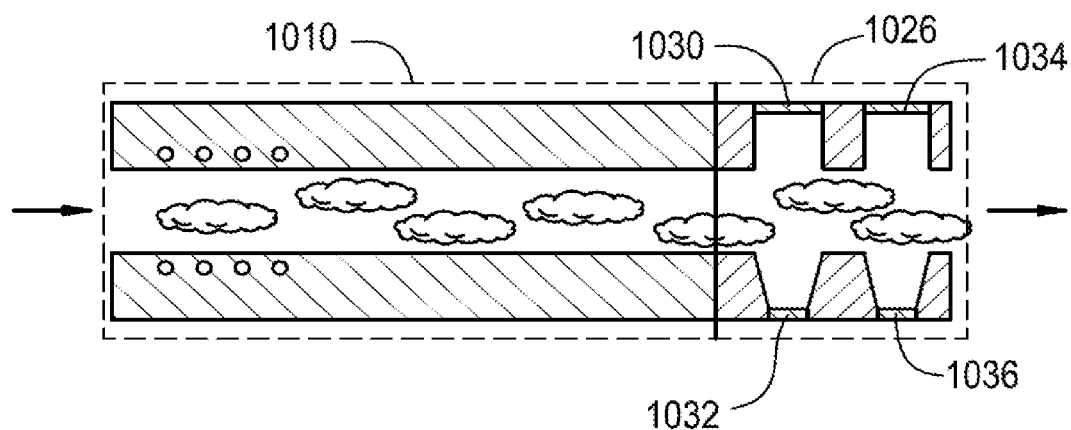

In another embodiment the vapor sensor may be used to identify vapor flow rate by having a dual vapor sensor set up. For example, as illustrated in FIG. 10, an inhalation device may include an atomizer portion 1010 and a vapor sensing unit 1026. The vapor sensing unit 1026 may have a first light sensor 1030, a first light source 1032, a second light sensor 1034, and a second light source 1036.

As shown in FIG. 10, vapor would flow past the two vapor light sensors 1030 and 1034 that may be positioned in such a way that the vapor passes by the first sensor 1030 before passing by the second sensor 1034. Both sensors 1030 and 1034 would record the passing vapor intensity profile, and the detailed fluctuations that naturally occur during in vaporization flow. The two sensors 1030 and 1034 may record essentially the same profiles and details, however at different times due to their different positions in the pathway. The microprocessor may analyze the two profiles, find matching reference points in both, and calculate a time offset. Based on the calculated time offset and physical distance between these sensors, the flow rate may be calculated. FIG. 12 for example, shows these two profiles over time. In FIG. 12, the profile of the first sensor 1030 is the solid line and the profile of the second sensor 1034 is the broken line.

In another embodiment, the inhalation devices described herein can be connected to a mobile device such as a smartphone or tablet and interfaced with a software application. The software application can record the doses that the user has inhaled and record the user's dosage experience. This information can be analyzed by the software to track and optimize the user's experience with the substance inhaled. To help improve analysis, the user could also enter personal information such as ailments, pains, weight and food intake. The information recorded can be used to accurately monitor a user's intake details and may be submitted to a doctor for review and/or diagnostic evaluation.

The application could also connect with other users via the internet. This could be used to share experiences, receive recommendations, and network with a community of users. The application may also be used as an ecommerce platform to purchase dosage capsules, or vaporizer equipment. The platform could offer specific substances based on a user's rated experience. Another enhanced use might be finding other users within geographic locations that may allow for social interactions and meetings. These enhanced services may be integrated with others over the internet.

The vaporizer device could also be locked by the user via the application. This could be used as a safety feature against undesired use (by children or others). There could be a customizable lock setting to enhance safety or limit usage for those with low self control.

While embodiments have been described herein with a wick and heating element, other suitable methods of vaporizing a substance could be utilized without departing from the scope of this disclosure. For example, the substance to be vaporized could be placed in a chamber or oven. The oven can be a small cup made of metal, where a user could place the substance. The oven would then heat up and vaporize the substance. Any vapor produced can exit the oven and flow to the user when the user inhales.

While embodiments have been illustrated and described herein, it is appreciated that various substitutions and changes in the described embodiments may be made by those skilled in the art without departing from the spirit of this disclosure. The embodiments described herein are for illustration and not intended to limit the scope of this disclosure.

As an example and not by way of limitation, the processor and memory may provide the above described functionalities as a result of the processor(s) (e.g., integrated circuit, ASIC) executing software embodied in one or more tangible, computer-readable media. Such computer-readable media can be media associated with user-accessible mass storage memory as discussed above. The software implementing various embodiments of the present disclosure can be stored in such devices and executed by the processor. A computer-readable medium can include one or more memory devices or chips, according to particular needs. The software can cause the processor to execute particular processes or particular parts of particular processes described herein, including defining data structures stored in the memory (e.g., RAM) and modifying such data structures according to the processes defined by the software. In addition or as an alternative, the processor can provide functionality as a result of logic hardwired or otherwise embodied in a circuit, which can operate in place of or together with software to execute particular processes or particular parts of particular processes described herein. Reference to software can encompass logic, and vice versa, where appropriate. Reference to a computer-readable media can encompass a circuit (such as an integrated circuit (IC)) storing software for execution, a circuit embodying logic for execution, or both, where appropriate. The present disclosure encompasses any suitable combination of hardware and software.

While this disclosure has described several exemplary embodiments, there are alterations, permutations, and various substitute equivalents, which fall within the scope of the disclosure. It will thus be appreciated that those skilled in the art will be able to devise numerous devices, systems and methods which, although not explicitly shown or described herein, embody the principles of the disclosure and are thus within the spirit and scope thereof.

The invention claimed is:

1. An inhalation device for providing metering information regarding vaporized substance inhalation to a user, the inhalation device comprising:
a main body comprising a channel through which the vaporized substance can flow, the main body including an inlet that is a first opening and an outlet that is a second opening;
a light source that emits light and that is positioned inside of the channel;
a light sensor that senses an intensity of the light emitted from the light source;
a puff detecting element configured to send an electric signal when a puff is detected;
a memory; and
a processor or circuit configured to:
when the electric signal indicating that the puff has been detected by the puff detecting element is received, perform a series of steps, the series of steps including:
starting a heating element to begin vaporizing a substance;
extracting, from the memory, a predetermined known flow rate that is stored in the memory in advance, the predetermined known flow rate being a known flow rate of either the inhalation device itself or a portion of the channel of the inhalation device;
determining, based on the extracted predetermined known flow rate and information received from the light sensor regarding the intensity of the light emitted from the light source, an amount of vaporized substance that have been produced;
accumulating, in the memory, as a total amount produced, the determined amount of vaporized substance that has been produced in the memory as a total amount produced; and
when the accumulated total amount produced reaches a predetermined threshold dosage amount: (i) shutting off the heating element or (ii) sending, to an indicator, a signal indicating that the predetermined threshold dosage amount of the vaporized substance has been consumed, wherein the determining of the amount of the vaporized substance includes: obtaining a predetermined number of readings from the light sensor in a predetermined amount of time, determining a percentage, which is a vapor factor, as a ratio of an expected amount of production for the predetermined amount of time to an actual amount of vapor produced over the predetermined amount of time, multiplying the predetermined amount of time by the vapor factor at that time, and determining a total amount that has been consumed by accumulating each multiplication product.

2. The inhalation device of claim 1, wherein
the light source and the light sensor are positioned in the channel such that the vaporized substance can flow past the light sensor and the light source, and
the puff detecting element includes at least one of: a fin or propeller positioned in a flow pathway to spin as a mixture of vapor and air passes, a heated wire positioned in the flow pathway such that passing air will create a drop in the temperature of the heated wire, a temperature sensor located downstream from the heating element as to measure the temperature of the passing air, and a puff sensor positioned on a mouthpiece such that when the user's lips touch the mouthpiece, the puff is detected.

3. The inhalation device according to claim 1, wherein the processor or circuit is further configured to: determine the amount of vaporized substance that has been produced based on a correlation between the light intensity and a mixture of vapor and air.

4. The inhalation device according to claim 3, wherein the correlation is based on a graph of a value percent drop in the light intensity versus a percentage of vapor in the mixture of vapor and air.

5. The inhalation device according to claim 3, wherein the correlation is based on a graph of a value percent drop in the light intensity versus a percentage of cannabis oil vapor in the mixture of vapor and air.

6. The inhalation device of claim 1, wherein
the channel includes a first channel portion and a second channel portion,
the processor or circuit uses data from the light sensor to meter consumption of the vaporized substance, and
the predetermined known flow rate that is stored in advance is based on a length of the second channel portion.

7. The inhalation device of claim 1, wherein
the indicator informs the user when a dose of the substance has been inhaled, and
the indicator includes at least one of: an audio signal, a visual signal, a visual display, a vibrator or a transmitter that sends information to an external device.

8. The inhalation device of claim 1, wherein the first opening is configured to allow entry of air into the inhalation device such that the air flows at a substantially constant rate.

9. The inhalation device of claim 8, wherein the processor or circuit, using the substantially constant rate and data from the light sensor, is configured to meter an amount of vapor consumed by the user.

10. The inhalation device of claim 1, wherein
the channel includes a first channel portion and a second channel portion, and
when the user inhales, the vapor will flow in the first channel portion and through the second channel portion before flowing through the outlet, and
the light source and the light sensor are positioned for sensing concentration of the vaporized substance that flows in the second channel portion.

11. The inhalation device of claim 10, wherein to perform the sensing of the concentration, the light source and the light sensor are positioned such that they are attached at respective ends of the second channel portion.

12. The inhalation device of claim 11, wherein the second channel portion is relatively provided at a level below the first channel portion.

13. The inhalation device of claim 11, wherein the inhalation device is configured to cause the vapor to:
upon exiting the first channel portion, travel in a downward direction to and into the second channel portion, and
upon exiting the second channel portion, travel in a direction upwards to the outlet.

14. The inhalation device of claim 1, wherein the inlet comprises at least two sidewalls, and a flow rate through the channel is limited by surface tension and friction between air and the at least two sidewalls.

15. The inhalation device of claim 1, further comprising a plunger that is positioned at the inlet and is configured to move in an axial direction to limit airflow into the inhalation device.

16. The inhalation device of claim 1, wherein the processor or circuit is configured to at least one of: produce discreet pulses of vapor at a preset frequency and or produce vapor in a pattern of a sine wave.

17. The inhalation device of claim 1, wherein
the channel includes a first channel portion and a second channel portion,
when the user inhales, the vaporized substance will flow in the first channel portion and through the second channel portion before flowing through the outlet,
the light source and the light sensor are positioned for sensing concentration of the vaporized substance that flows in the second channel portion,
to perform the sensing of the concentration, the light source and the light sensor are positioned such that they are attached at respective ends of the second channel portion, and
where a vapor flow direction in the first channel portion is an X-axis of a local coordinate grid, a ceiling of the second channel portion is completely or partially below the first channel portion, where below means on a different Y-coordinate plane of the local coordinate grid that has the X-axis corresponding to the vapor flow direction in the first channel portion.

18. An inhalation device for providing metering information regarding vaporized substance inhalation to a user, the inhalation device comprising:
a main body comprising a channel through which the vaporized substance can flow, the main body including an inlet that is a first opening and an outlet that is a second opening;
a light source that emits light and that is positioned inside of the channel;
a light sensor that senses an intensity of the light emitted from the light source;
a puff detecting element configured to send an electric signal when a puff is detected;
a memory; and
a processor or circuit configured to:
when the electric signal indicating that the puff has been detected by the puff detecting element is received, perform a series of steps, the series of steps including:
starting a heating element to begin vaporizing a substance;
extracting, from the memory, a predetermined known flow rate that is stored in the memory in advance, the predetermined known flow rate being a known flow rate of either the inhalation device itself or a portion of the channel of the inhalation device;
determining, based on the extracted predetermined known flow rate and information received from the light sensor regarding the intensity of the light emitted from the light source, an amount of vaporized substance that have been produced;
accumulating, in the memory, as a total amount produced, the determined amount of vaporized substance that has been produced; and
when the accumulated total amount produced reaches a predetermined threshold dosage amount:
(i) shutting off the heating element or (ii) sending, to an indicator, a signal indicating that the predetermined threshold dosage amount of the vaporized substance has been consumed, wherein
the channel includes a first channel portion and a second channel portion,
when the user inhales, the vaporized substance will flow in the first channel portion and through the second channel portion before flowing through the outlet,
the light source and the light sensor are positioned for sensing concentration of the vaporized substance that flows in the second channel portion,
to perform the sensing of the concentration, the light source and the light sensor are positioned such that they are attached at respective ends of the second channel portion, and
the respective ends of the second channel portion are parallel to each other and perpendicular to a vapor flow direction in the first channel portion.

19. The inhalation device of claim 18, wherein the determining of the amount of vaporized substance includes:
obtaining a predetermined number of readings from the light sensor in a predetermined amount of time;
determining a percentage, which is a vapor factor, as a ratio of an expected amount of production for the predetermined amount of time to an actual amount of vapor produced over the predetermined amount of time;
multiplying the predetermined amount of time by the vapor factor at that time; and
determining a total amount that has been consumed by accumulating each multiplication product.

* * * * *